US011123390B2

(12) United States Patent
Alansari

(10) Patent No.: US 11,123,390 B2
(45) Date of Patent: Sep. 21, 2021

(54) METHOD FOR TREATING VITILIGO

(71) Applicant: KUWAIT UNIVERSITY, Safat (KW)

(72) Inventor: Mohammad Abdulrahman Ali Alansari, Adailiyya (KW)

(73) Assignee: KUWAIT UNIVERSITY, Safat (KW)

( * ) Notice: Subject to any disclaimer, the term of this patent is extended or adjusted under 35 U.S.C. 154(b) by 468 days.

(21) Appl. No.: 16/134,092

(22) Filed: Sep. 18, 2018

(65) Prior Publication Data
US 2020/0085899 A1 Mar. 19, 2020

(51) Int. Cl.
| | |
|---|---|
| *A61K 36/487* | (2006.01) |
| *A61P 17/00* | (2006.01) |
| *A61K 9/00* | (2006.01) |
| *A61K 36/185* | (2006.01) |
| *A61K 36/23* | (2006.01) |
| *A61K 36/28* | (2006.01) |
| *A61K 36/29* | (2006.01) |
| *A61K 36/482* | (2006.01) |
| *A61N 5/06* | (2006.01) |

(52) U.S. Cl.
CPC .......... *A61K 36/487* (2013.01); *A61K 9/0014* (2013.01); *A61K 36/185* (2013.01); *A61K 36/23* (2013.01); *A61K 36/28* (2013.01); *A61K 36/29* (2013.01); *A61K 36/482* (2013.01); *A61N 5/062* (2013.01); *A61N 5/0616* (2013.01); *A61P 17/00* (2018.01); *A61N 2005/0661* (2013.01); *G01N 2800/207* (2013.01)

(58) Field of Classification Search
None
See application file for complete search history.

(56) References Cited

U.S. PATENT DOCUMENTS

| | | | |
|---|---|---|---|
| 2001/0044422 A1 | 11/2001 | Zhao | |
| 2003/0072813 A1 | 4/2003 | Zhao | |
| 2012/0238506 A1* | 9/2012 | Msika | |
| 2012/0321579 A1* | 12/2012 | Edelson | |
| 2014/0056973 A1* | 2/2014 | Ma | |
| 2014/0073659 A1* | 3/2014 | Magilavy | |
| 2016/0235708 A1* | 8/2016 | Banjeri | |

FOREIGN PATENT DOCUMENTS

| | | |
|---|---|---|
| CN | 101099818 A | 1/2008 |
| CN | 101428098 A | 5/2009 |
| CN | 101461847 A | 6/2009 |
| CN | 101485770 A | 7/2009 |
| CN | 101632738 A | 1/2010 |
| CN | 101926857 A | 12/2010 |
| CN | 101940624 A | 1/2011 |
| CN | 101940695 A | 1/2011 |
| CN | 102228538 A | 11/2011 |
| CN | 103690766 A | 4/2014 |
| CN | 104083445 A | 10/2014 |
| CN | 104288440 A | 1/2015 |
| CN | 105287696 A | 2/2016 |
| CN | 106074778 A | 11/2016 |
| CN | 107335034 A | 11/2017 |

OTHER PUBLICATIONS

Khushboo (Psoralea corylifolia Linn.—"Kushtanashini", Pharacogn Rev Jul. 1, 2010) (Year: 2010).*
Dhanik (Clinical evaluation of the efficacy of Shvitrahara kashaya and lepa in vitiligo, AYU Jan.-Mar. 2011) (Year: 2011).*
Chang (Antioxidant activity of Saussurea lappa C.B. Clarke Roots, Preventive Nutrition and Food Science, Dec. 2012, 17(4):306-309) (Year: 2012).*
https://wordanova.com/health-benefits-of-pomegranate-you-didnt-know/, Wordanova, Feb. 19, 2018) (Year: 2018).*
Rahimi-Madiseh (Berberis vulgaris: specifications and traditional uses, IJBMS, Apr. 14, 2017) (Year: 2017).*
NDTV (https://www.ndtv.com/health/world-vitiligo-day-2018-10-effective-home-remedies-to-treat-vitiligo-1872328, Jun. 24, 2018) (Year: 2018).*
El Ouariachi (Chemical composition and antioxidant activity of essential oils and solvent extracts of Ptychotis verticillata from Moroco, Food and Chemical Toxicology, vol. 49, Feb. 2011) (Year: 2011).*
International Search & Written Opinion for PCT/IB2019/057674, dated Feb. 3, 2020.
Gianfaldoni, S. et al., "Herbal Compounds for the Treatment of Vitiligo: A Review," Open Access Maced J Med Sci. 6(1): pp. 203-207, (Jan. 25, 2018).
Dhanik, A., et al., "Clinical evaluation of the efficacy of Shitrahara kashaya and lepa in vitiligo," Medknow Publications and Media Pvt. Ltd, 32(1): pp. 66-69, (2011).
Sharma, G. C. et al., "Ethanomedicinal trends in Indian tradition for treatment of vitiligo," J. Med. Plants Res. 6(10): pp. 1827-1833, (2012).
Baccarin, T. and Lemos-Senna, E., "Potential Application of Nanoemulsions for Skin Delivery of Pomegranate Peel Polyphenols," AAPS Pharma. Sci. Tech. 18(8): pp. 3307-3314, (2017).
Di Nardo, V. et al., "Functional nutrition as integrated approach to vitiligo management," Dermatol. Ther. 32(4): e12625, (Epub Aug. 28, 2018).

(Continued)

*Primary Examiner* — Susan Hoffman
*Assistant Examiner* — Jacob A Boeckelman
(74) *Attorney, Agent, or Firm* — Nath, Goldberg & Meyer; Richard C. Litman

(57) ABSTRACT

A first embodiment of a composition for treating vitiligo includes *Cassia tora* powder, *Saussurea lappa* root powder, *Punica granatum* L. (pomegranate) peels powder, and *Psoralea corylifolia* black seed powder. A second embodiment of a composition for treating vitiligo can include *Cassia tora* powder, *Saussurea lappa* root powder, *Punica granatum* L. (pomegranate) peels powder, *Berberries* (or *Berberis*) *vulgaris* root powder, red clay (with trace copper), and *Ptychotis verticillata* root powder. Topical administration of the first composition followed by UV radiation exposure can facilitate inducing melanogenesis as well as generating ROS. Topical administration of the second composition following the UV radiation exposure can scavenge the ROS generated by the first composition.

7 Claims, 1 Drawing Sheet

(56) References Cited

OTHER PUBLICATIONS

Zahara, K. et al., "A review of therapeutic potential of Saussurea lappa—An engangered plant from Himalaya," Asian Pac. J. Trop. Med. 7(Supp 1): pp. S60-S69, (2014).

Zaidi, K. U. et al., "Natural melanogenesis stimulator a potential tool for the treatment of hypopigmentation disease," Int. J. Mol. Biol. Open Access 2(1): pp. 37-40, (2017).

Lakhani, D. M. and Deshpande, A. S., "Various Treatments for Vitiligo: Problems Associated and Solutions," J. App. Pharma. Sci. 4(11): pp. 101-105, (2014).

Pacheco-Palencia et al., "Protective effects of standardized pomegranate (*Punica granatum* L.) polyphenolic extract in ultraviolet-irradiated human skin fibroblasts," J. Agric. Food Chem., 2008, 56 (18), pp. 8434-8441. (abstract only).

Khushboo et al., "Psoralea corylifolia Linn.—'Kushtanashini'" Pharmacogn Rev., Jan.-Jun. 2010; 4(7): 69-76, 10 pages.

"Chakramarda (Cassia tora) Information, Benefits, Uses and side-effects," Bimbima website, © 2017, 14 pages.

"Costus root essential oil facts and health benefits," Health Benefits Times website, © 2017, 8 pages.

"Barberry—Health Benefits and Side Effects," The Herbal Resource website, © 2018, 11 pages.

El Ouarlachi et al., "Chemical composition and antioxidant activity of essential oils and solvent extracts of Ptychotis verticillata from Morocco," Food Chem Toxicol., Feb. 2011; 49(2): 533-6.

\* cited by examiner

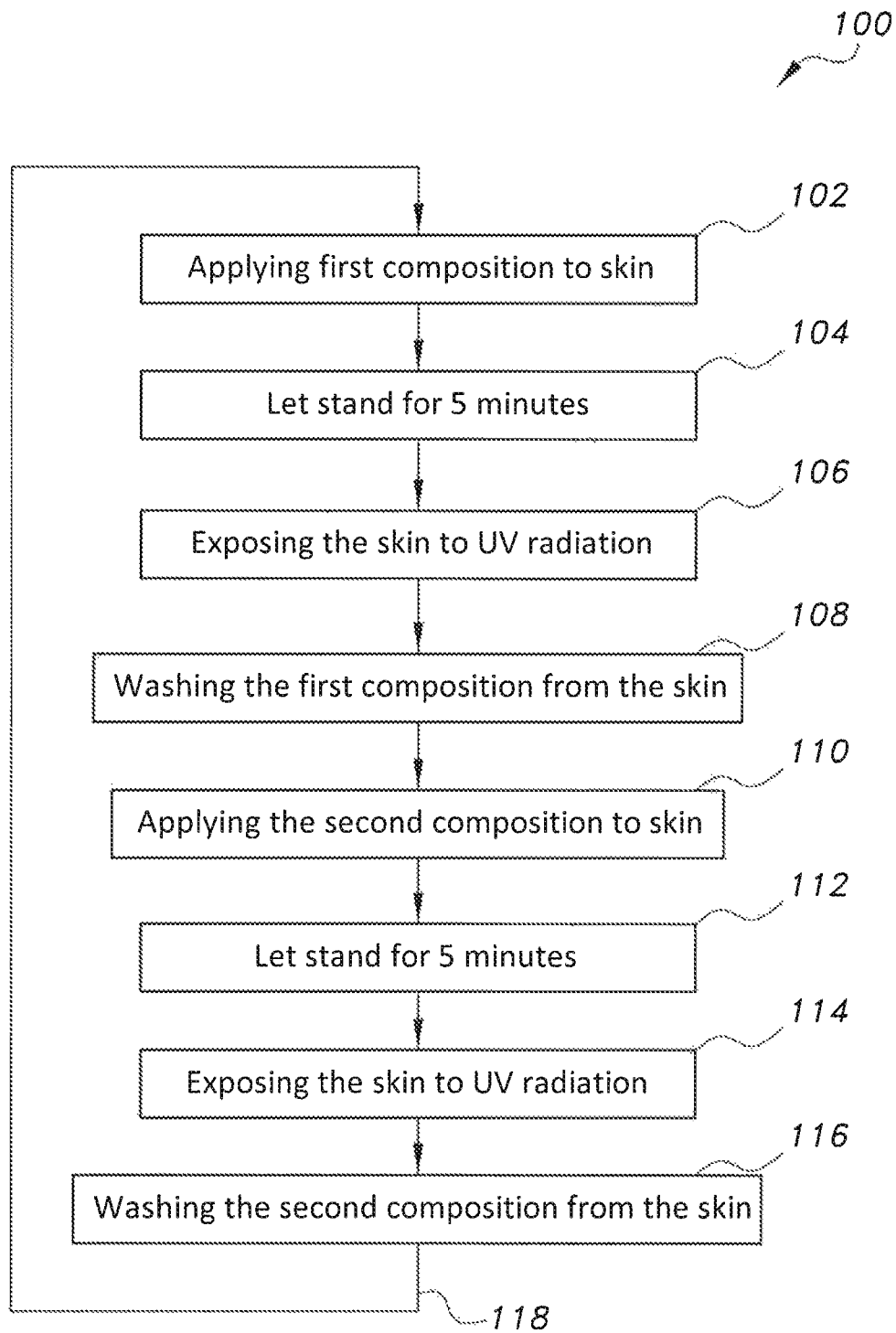

METHOD FOR TREATING VITILIGO

BACKGROUND

1. Field

The disclosure of the present patent application relates to topical medicines and protocols, and particularly to a vitiligo treatment medicine and protocol based on separate pulse administration of vitiligo treatment compositions in addition to phototherapy.

2. DESCRIPTION OF THE RELATED ART

Vitiligo is a multigene and multifactorial disorder that results in the depigmentation of the skin. Current treatments for vitiligo include UV (ultra-violent) radiation therapy. UV radiation induces melanin production in the skin through melanogenesis. Normal melanogenesis occurs in melanocytes, where tyrosine is converted to melanin by the enzyme tyrosinase and copper co-factor. UV radiation also produces reactive oxygen species (ROS). Typically, ROS is scavenged by the body's natural antioxidants. Patients suffering from vitiligo, however, have decreased natural antioxidant activity and increased reactive oxygen species (ROS). Increased ROS and low levels of self-antioxidants can cause oxidative damage to melanocytes. Excessive ROS can cause changes in lipids and protein structure in a way that triggers antibody production against melanocytes. As such, while conventional UV radiation therapies can generate melanin, the excessive ROS that can also be generated can damage pigment cells.

Phototherapy can also generate peroxynitrite. Peroxynitrite can attack the phenol ring of amino acid tyrosine, the building block of melanin. Accordingly, peroxynitrite can inhibit or prevent melanin production.

Thus, a composition and method for treating vitiligo solving the aforementioned problems is desired.

SUMMARY

A first embodiment of a composition for treating vitiligo includes *Cassia tora* powder, *Saussurea lappa* root powder, *Punica granatum* L. (pomegranate) peels powder, and *Psoralea corylifolia* black seed powder. The first embodiment can include one part *Psoralea corylifolia* black seed powder, five parts *Cassia tora* powder, three parts *Saussurea lappa* root powder, and ten parts *Punica granatum* L (pomegranate) peels powder.

A second embodiment of a composition for treating vitiligo can include *Cassia tora* powder, *Saussurea lappa* root powder, *Punica granatum* L. (pomegranate) peels powder, *Berberries* (or *Berberis*) *vulgaris* root powder, red clay (with trace copper), and *Ptychotis verticillata* root powder. The second embodiment can include two parts *Berberries* (or *Berberis*) *vulgaris* root powder; three parts *Cassia tora* powder; one part red clay (with trace copper); two parts *Saussurea lappa* root extract; two parts *Ptychotis verticillata* root powder; and two parts *Punica granatum* L peels powder.

A method of treating vitiligo can include applying the first embodiment of the composition to the patient's skin, exposing the skin to a UV radiation source, e.g., sunlight, after application of the first embodiment of the composition, washing the first embodiment of the composition from the skin, applying the second embodiment of the composition to the skin, and exposing the skin to the UV radiation again after application of the second embodiment of the composition. The method can be repeated until desired results are achieved. The first embodiment of the composition can be allowed to remain on the skin for a short period of time, for example about 5 minutes, prior to exposing the treated skin to UV radiation. Similarly, the second embodiment of the composition can be allowed to remain on the skin for a short period of time, for example about 5 minutes, prior to exposing the treated skin to UV radiation. The exposure to sunlight or UV radiation can range from about 30 seconds to about 15 minutes, depending upon the sensitivity of the skin. The first composition can facilitate inducing melanogenesis as well as generating ROS. The second composition can scavenge the ROS generated by the first composition.

These and other features of the present disclosure will become readily apparent upon further review of the following specification and drawings.

BRIEF DESCRIPTION OF THE DRAWING

The sole FIGURE is a block diagram of the vitiligo treatment protocol.

Similar reference characters denote corresponding features consistently throughout the attached drawing.

DETAILED DESCRIPTION OF THE PREFERRED EMBODIMENTS

A method for treating vitiligo can include topically administering a first embodiment of a vitiligo treatment composition ("first composition") to the affected skin of a patient suffering from vitiligo, exposing the skin treated with the first composition to UV radiation, washing the first composition off of the treated skin, administering a second embodiment of a vitiligo treatment composition ("second composition") to the affected skin of the patient, and exposing the skin treated with the second composition to UV radiation. The first composition and the second composition both include *Cassia tora* powder, *Saussurea lappa* root powder, and *Punica granatum* L. (pomegranate) peels powder. The first composition further includes *Psoralea corylifolia* black seed powder. The second composition further includes *Berberries* (or *Berberis*) *vulgaris* root powder, red clay (with trace copper), and *Ptychotis verticillata* root powder. In an embodiment, the first composition includes one part *Psoralea corylifolia* black seed powder, five parts *Cassia tora* powder, three parts *Saussurea lappa* root powder, and ten parts *Punica granatum* L (pomegranate) peels powder. In an embodiment, the second composition includes two parts *Berberries* (or *Berberis*) *vulgaris* root powder, three parts *Cassia tora* powder, one part red clay (with trace copper), two parts *Saussurea lappa* root extract, two parts *Ptychotis verticillata* root powder, and two parts *Punica granatum* L. peels powder.

The first embodiment of the composition can be allowed to remain on the skin for a short period of time, for example about 5 minutes, prior to exposing the treated skin to UV radiation. The second embodiment of the composition can be allowed to remain on the skin for a short period of time, for example about 5 minutes, prior to exposing the treated skin to UV radiation. The exposure to sunlight or UV radiation can range from about 30 seconds to about 10 minutes, depending upon the sensitivity of the skin.

The first composition can facilitate inducing melanogenesis as well as generating ROS. The second composition can scavenge the ROS generated by the first composition. *Psoralea* extract is a known photosynthesizer. *Saussurea lappa* has natural immunomodulatory effects and can, thereby, prevent an immune response in the event of excessive ROS production. *Cassia tora* can serve as a peroxinitrite scavenger to protect the phenol ring of tyrosine from oxidative damage. Red clay with copper co-factor can also facilitate melanogenesis.

It is believed that the pulse application of the first composition, which includes photosensitive compounds, followed by a very short duration of UV radiation exposure, and subsequent application of the second composition, which includes antioxidants, can trigger melanogenesis while avoiding excessive/cascade of ROS reactions.

The first composition can be prepared by mixing one part *Psoralea corylifolia* black seed powder, five parts *Cassia tora* powder, three parts *Saussurea lappa* root powder, and ten parts *Punica granalum* L (pomegranate) peels powder to provide a first powder mixture, and adding water to the first powder mixture, e.g., in a 1:4 volume ratio, to provide the first composition. The second composition can be prepared by mixing two parts *Berberries* (or *Berberis*) *vulgaris* root powder, three parts *Cassia tora* powder, one part red clay (with trace copper), two parts *Saussurea lappa* root extract, two parts *Ptychotis verticillata* root powder, and two parts *Punica granatum* L. peels powder to provide a second powder mixture, and adding water to the second powder mixture, e.g., in a 1:4 volume ratio, to provide the second composition.

As shown in the sole FIGURE, an exemplary treatment protocol or method of vitiligo treatment 100 according to the present teachings includes a first step 102 of applying the first composition to the skin, waiting about 5 minutes 104, exposing the skin to sunlight (or another UV light source) in step 106, washing the first composition from the skin 108, applying the second composition to the skin 110, waiting about 5 minutes 112, exposing the skin to sunlight 114, and washing the second composition from the skin 116. The initial exposure time in step 106 and step 112 can be about 30 seconds, but can be increased by 30 seconds every 3 days to a maximum of 15 minutes, if there is no skin redness or phototoxicity. As shown by the line 118, after step 116, the treatment method 100 returns to the first step 102 to be repeated as necessary.

A composition for treating vitiligo, according to a first embodiment, can include *Psoralea corylifolia* black seed powder, *Cassia tora* powder, *Saussurea lappa* root powder, and *Punica granatum* L (pomegranate) peels powder. For example, the composition can include one part *Psoralea corylifolia* black seed powder, five parts *Cassia tora* powder, three parts *Saussurea lappa* root powder, and ten parts *Punica granatum* L (pomegranate) peels powder.

A composition for treating vitiligo, according to a second embodiment can include *Berberries* (or *Berberis*) *vulgaris* root powder, *Cassia tora* powder, red clay (with trace copper); *Saussurea lappa* root extract, *Ptychotis verticillata* root powder, and *Punica granatum* L peels powder. For example, the composition can include two parts *Berberries* (or *Berberis*) *vulgaris* root powder, three parts *Cassia tora* powder, one part red clay (with trace copper), two parts *Saussurea lappa* root extract, two parts *Ptychotis verticillata* root powder, and two parts *Punica granatum* L. peels powder.

The present teachings are illustrated by the following examples.

Example 1

A 32 year old male patient with non-segmental vitiligo (NSV) was treated according to the protocol set forth in the sole FIGURE. The treatment was administered to the skin of the patient in the hip, neck, arm, hand and knee areas. The treatment was provided from July 2016 to December 2017. In October of 2016, the neck area showed repigmentation and by 19 Jan. 2017, the neck area was almost completely cured. The right hand of the patient showed 10-15% repigmentation by October 2016. Hands are generally more difficult to treat for vitiligo. The left arm area showed 70-80% repigmentation by October 2016 and by January 2017 the left arm area had 95% repigmentation. The hip area of the patient showed improvement within two weeks and more than 60-70% repigmentation between Mar. 8, 2017 and Dec. 6, 2017. The knee of the patient showed very good repigmentation at week 9 and week 15 of the study, particularly around the hair follicles.

Example 2

A 35 year old male patient with segmental vitiligo (SV) on his lips was treated according to the protocol set forth in the sole FIGURE. The lips are a very difficult area to treat vitiligo and most treatment methods are ineffective. Within 10 weeks the SV was almost completely cured.

Example 3

A 32 year old female patient with progressive NSV on her left arm was treated according to the protocol set forth in the sole FIGURE. Within one month, some repigmentation had occurred.

Example 4

A 20 year old female patient with progressive NSV just starting on her shoulder, left eyelid and left wrist was treated according to the protocol set forth in the sole FIGURE. The eyelids are also a very difficult area to treat vitiligo and most treatment methods are ineffective. The treatment achieved good results.

Example 5

A 26 year old male patient with SV around the mouth area was treated according to the protocol set forth in the sole FIGURE. In addition to treating the vitiligo, generally improved skin health was observed including a reduction of acne on the patient's face. Prior, conventional UV treatment had not been successful.

Example 6

A 38 year old female patient with NSV on her legs was treated according to the protocol set forth in the sole FIGURE. This patient was a smoker. Generally, smokers are less responsive to NSV treatment. After three months of treatment, improvement was limited, but after five months, repigmentation was visible and the area of the vitiligo was reduced.

Example 7

A 10 year old female patient with progressive NSV on her eyelids was treated according to the protocol set forth in the sole FIGURE. After treatment, complete repigmentation of the eyelids was observed.

Example 8

A 37-year old female patient with progressive NSV on her forehead was treated according to the protocol set forth in the sole FIGURE. Repigmentation of the forehead was observed within 20 days of treatment. Within 30 days, almost complete repigmentation of the forehead was observed. General skin health improvement was also observed including a decrease in acne.

It is to be understood that a method for treating vitiligo is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A two-phase method for treating vitiligo, comprising the steps of:
  a first phase of photosensitive compounds, the first phase consisting of the steps of:
    applying a first composition to an affected skin of a patient suffering from vitiligo, the first composition comprising *Psoralea corylifolia* black seed powder, *Cassia tora* powder, *Saussurea lappa* root powder, and *Punica granatum* L. (pomegranate) peels powder;
    exposing the skin treated with the first composition to a UV radiation source for a first period of time; and
    washing the first composition from the affected skin;
  a second phase of antioxidant compounds, the second phase consisting of the steps of:
    applying a second composition to the affected skin, the second composition comprising *Berberries vulgaris* root powder, *Cassia tora* powder, red clay (with trace copper), *Saussurea lappa* root extract, *Ptychotis verticillata* root powder, and *Punica granatum* L. peels powder;
    exposing the skin treated with the second composition to a UV radiation source for a second period of time; and
    washing the second composition from the affected skin.

2. The method according to claim 1, wherein the first composition comprises:
  one part of the *Psoralea corylifolia* black seed powder;
  five parts of the *Cassia Lora* powder;
  three parts of the *Saussurea lappa* root powder; and
  ten parts of the *Punica granatum* L. peels powder.

3. The method according to claim 1, wherein the second composition comprises:
  two parts of the *Berberries vulgaris* root powder;
  three parts of the *Cassia tora* powder;
  one part of the red clay;
  two parts of the *Saussurea lappa* root extract;
  two parts of the *Ptychotis verticillata* root powder; and
  two parts of the *Punica granatum* L. peels powder.

4. The method according to claim 1, wherein the first period of time ranges from 30 seconds to 15 minutes.

5. The method according to claim 4, wherein the first period of time is 30 seconds.

6. The method according to claim 1, wherein the second period of time ranges from 30 seconds to 15 minutes.

7. The method according to claim 6, wherein the second period of time is 30 seconds.

* * * * *